(12) United States Patent
Sleadd et al.

(10) Patent No.: US 8,748,639 B1
(45) Date of Patent: Jun. 10, 2014

(54) 3-AZIDO-2,4,6-TRINITROPHENOL, METHOD OF MAKING, AND METHOD OF TRANSFORMING

(75) Inventors: Bradley A. Sleadd, La Plata, MD (US); John Fronabarger, Sun Lakes, AZ (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 633 days.

(21) Appl. No.: 13/094,563

(22) Filed: Apr. 26, 2011

(51) Int. Cl.
  *C07C 247/16* (2006.01)
(52) U.S. Cl.
  USPC .............................................. 552/8
(58) Field of Classification Search
  USPC .............................................. 552/8
  See application file for complete search history.

(56) References Cited

U.S. PATENT DOCUMENTS 7,145,016 B1 * 12/2006 Fronabarger et al. ......... 548/126

* cited by examiner

*Primary Examiner* — Rebecca Anderson
*Assistant Examiner* — Karen Cheng
(74) *Attorney, Agent, or Firm* — Fredric J. Zimmerman

(57) ABSTRACT

The present disclosure sets forth the compound 3-azidopicric acid and a method of making the same. The method of producing 3-azidopicric acid is a two step reaction process of first reacting 3-aminopicric acid with sulfuric acid and sodium nitrite, and then reacting the result of the first step with phosphoric acid and sodium azide. Additionally described is a method of producing KDNP (4,6-dinitro-7-hydroxybenzofuroxan, potassium salt), by reacting 3-AzPA with potassium bicarbonate.

3 Claims, 5 Drawing Sheets

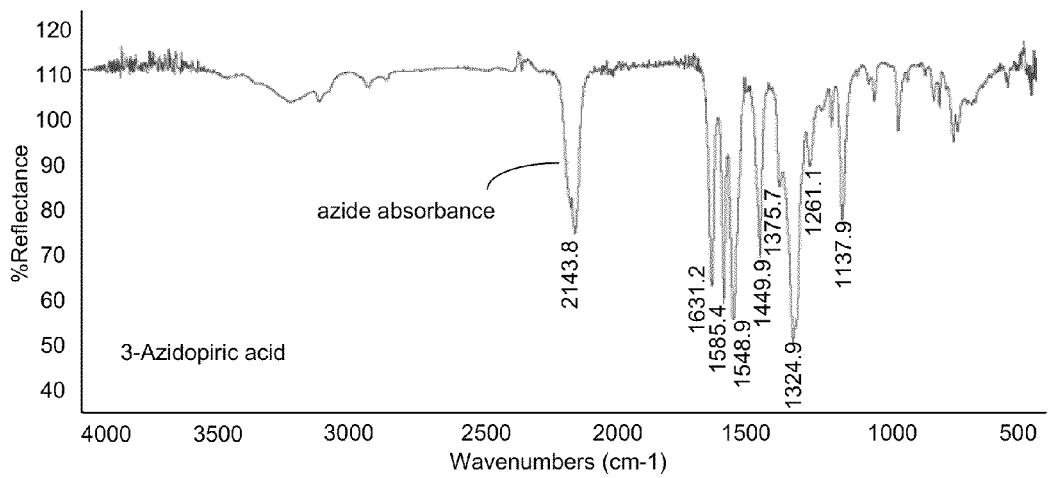
FIG. 1 3-AzPA FTIR
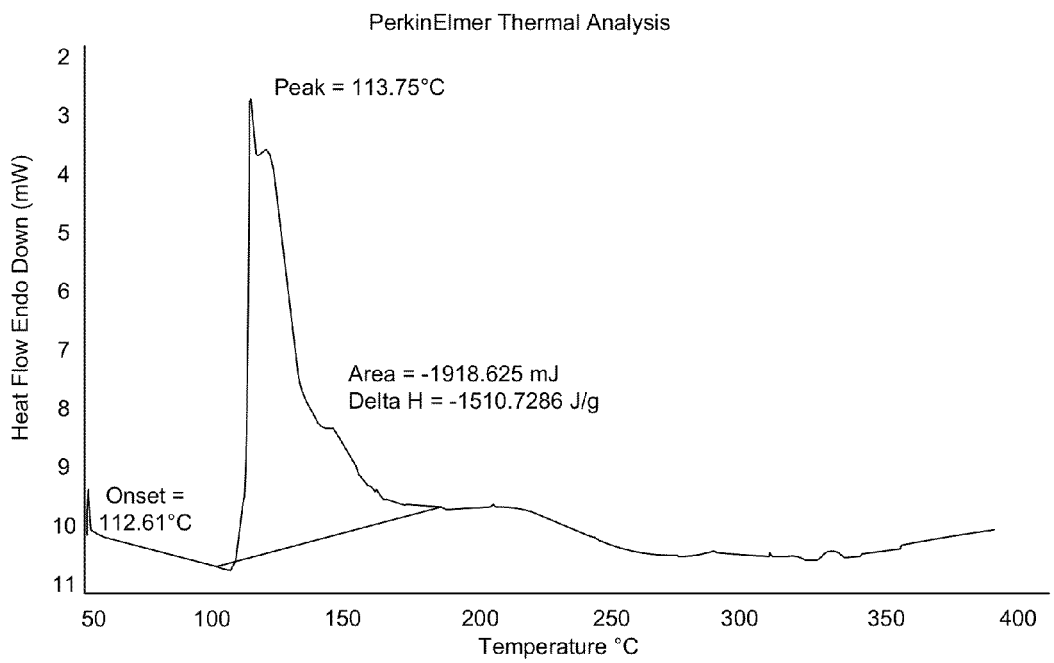
FIG. 2 3-AzPA DSC

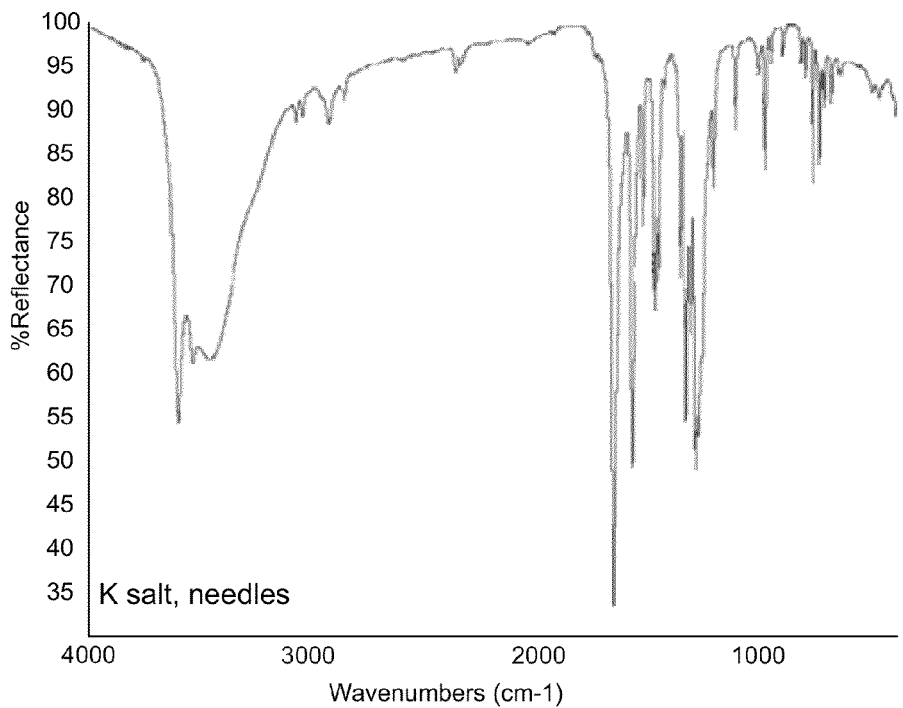
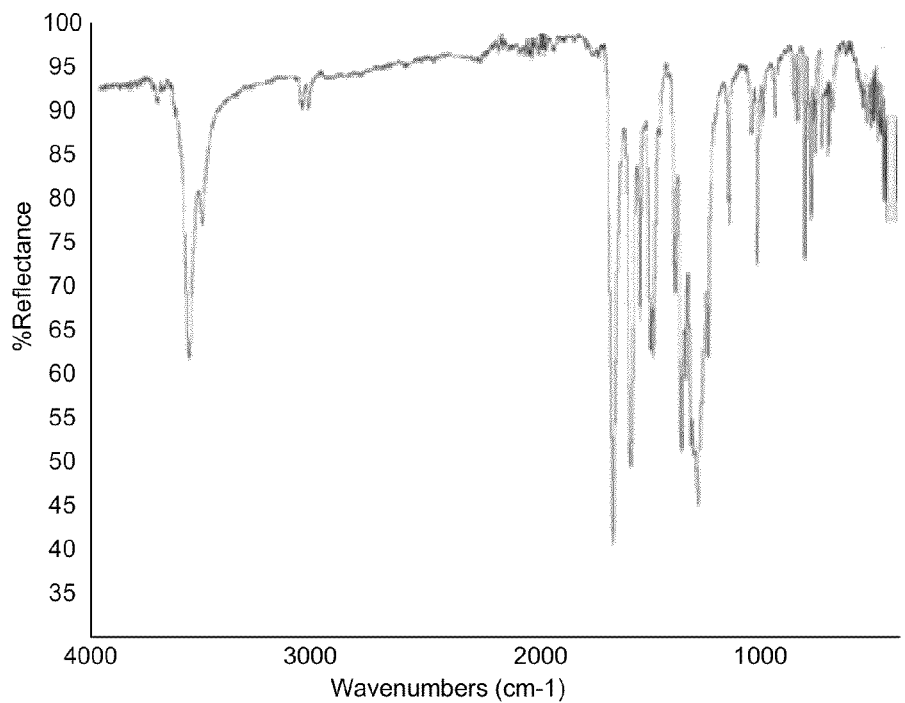
*FIG. 5*

3-AZIDO-2,4,6-TRINITROPHENOL, METHOD OF MAKING, AND METHOD OF TRANSFORMING

STATEMENT OF GOVERNMENT INTEREST

The present invention described herein may be manufactured and used by or for the Government of the United States of America for government purposes without the payment of any royalties thereon or therefore.

FIELD OF THE INVENTION

The present invention relates generally to a previously unreported compound 3-azido-2,4,6-trinitrophenol (3-azidopicric acid; 3-AzPA). And a method of making 3-AzPA is disclosed. Also disclosed is a method of transforming 3-AzPA into KDNP (4,6-dinitro-7-hydroxybenzofuroxan, potassium salt), a primary explosive material used in military ordnance.

BACKGROUND OF THE INVENTION

It has long been of interest to the energetic materials community to develop more environmentally friendly initiating compositions, since both of the most prevalent ingredients in use today, lead styphnate (LS) and lead azide (LA), release toxic lead compounds into the environment upon their decomposition. The challenge has been to identify non-toxic materials that have equivalent performance. Lead styphnate (LS) has been widely used in ordnance systems for many years. It is a reliable explosive material and its properties and manufacturing processes are well defined. Executive Order 12856 (1993) was issued to reduce or eliminate procurement of hazardous substances and chemicals by federal facilities. As a result, there have been a need to develop existing or new materials which would serve as a drop in replacement for LS and which incorporate no toxic or environmentally undesirable elements. Environmental health and safety regulations on lead containing materials are quite extensive and are likely to increase in severity in the future, along with compliance costs. The manufacture, use, demilitarization and disposal of LS (and ordnance containing them) are deeply impacted by these regulations, and lead-free alternatives to LS have been sought for many years.

U.S. Patent Application Publication No. 2009/0223401 to Fronabarger et al. discloses lead free primers wherein LS is replaced with KDNP (4,6-dinitro-7-hydroxybenzofuroxan, potassium salt). Disclosed therein is a three step process of making KDNP starting from m-bromoanisole, subjecting it to nitration, and reacting the resulting product with potassium azide ($KN_3$), thereby producing KDNP.

There is a need for a less expensive, environmentally friendly alternative synthesis to make KDNP. There is a vast surplus of Explosive D that must be demilitarized. Explosive D is ammonium picrate. If it can be recycled, instead of burned or other demilitarized process, the impact on the environment is friendlier.

BRIEF SUMMARY OF THE INVENTION

The present invention is based on the known conversion of ammonium picrate (Explosive D) to 3-aminopicric acid (3-APA) via vicarious nucleophilic substitution. Starting with 3-APA, the present invention converts it into 3-azidopicric acid (3-AzPA). 3-AzPA is a precursor to producing KDNP. Heretofore, 3-AzPA and a method of making it were not known.

In an exemplary embodiment, the present invention is the compound 3-azidopicric acid. In another exemplary embodiment, the present invention is the compound represented by the following formula

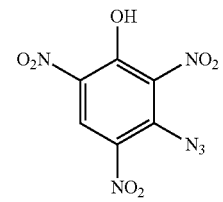

Chemical Formula: $C_6H_2N_6O_7$
Molecular Weight: 270.12.

In yet another exemplary embodiment of the present invention, a method of making 3-azidopicric acid includes a) reacting 3-aminopicric acid with sulfuric acid and sodium nitrite, and b) then reacting the result of step a) with phosphoric acid and sodium azide. In still yet another exemplary embodiment of the present invention, a method of making 4,6-dinitro-7-hydroxybenzofuroxan, potassium salt (KDNP) includes treating an aqueous solution of 3-azidopicric acid with potassium bicarbonate.

BRIEF DESCRIPTION OF THE DRAWINGS

FIG. 1 is a diagram of a Fourier Transform Infra-red Spectroscopy of 3-AzPA.

FIG. 2 is a diagram of a Differential Scanning Calorimetry for 3-AzPA.

FIG. 5 is a comparative diagram of Fourier Transform Infra-red Spectroscopy of a known KDNP sample vs. the diagram of Experimental Procedure 2.

DETAILED DESCRIPTION OF THE INVENTION

Figure 3:
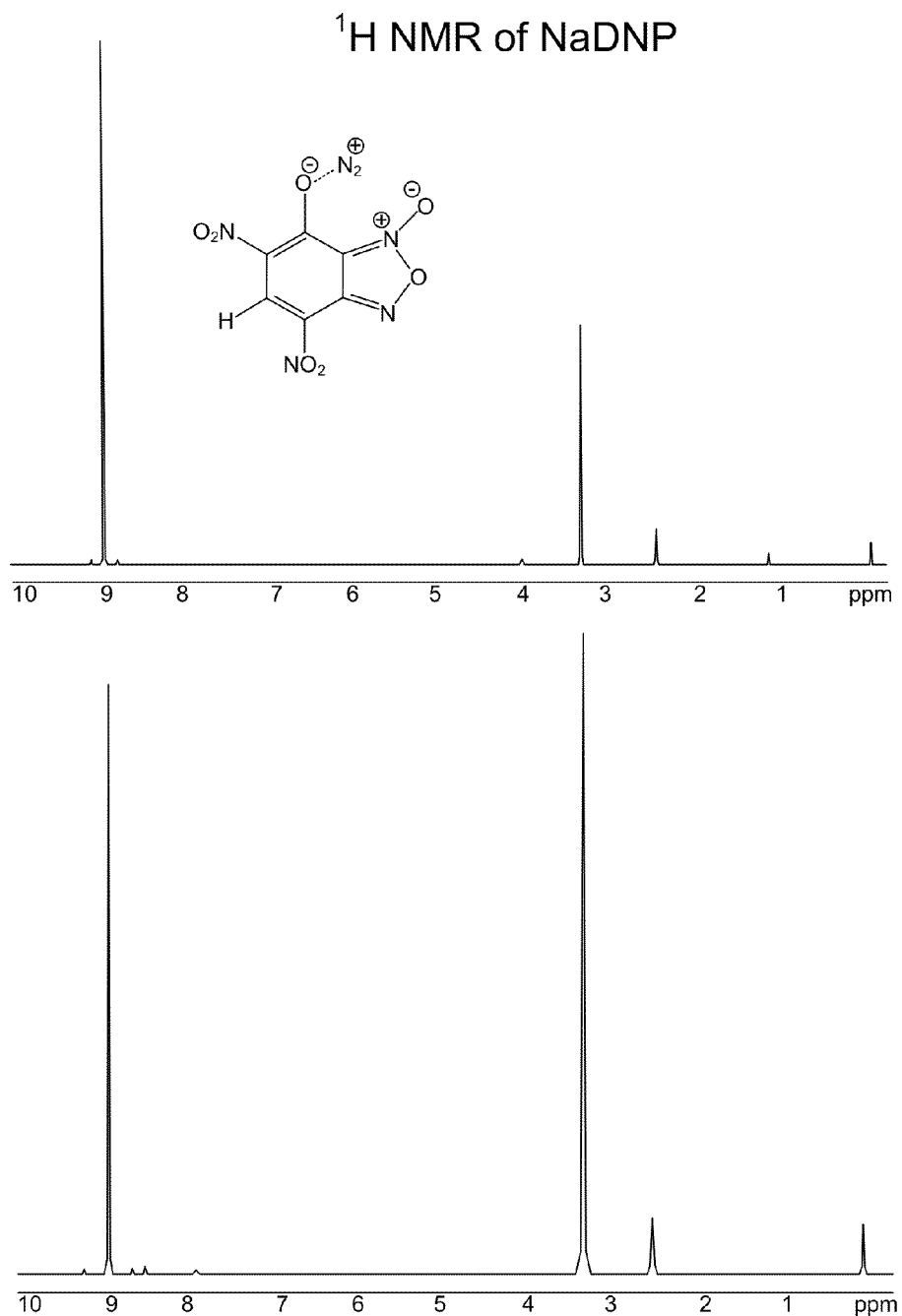
FIG. 3 is a comparative scan of a Nuclear Magnetic Resonance using $^1H$ for NaDNP vs. the scan of Experimental Procedure 2.

LS replacement, 7-hydroxy-4,6,dinitrobenzofuroxan, potassium salt (KDNP) has been successfully qualified as a primary explosive and identified as safe and suitable for service use and qualified for weapons development. KDNP has been successfully evaluated in a number of applications. However, it has only been produced in gram quantities and a scalable, less expensive, environmentally friendly synthetic route has not yet been identified. A process for the large scale manufacture of KDNP would accelerate the transition to replacement of LS system wide, reducing exposure to toxic materials both in theater and in training exercises. And with the present invention the transition would also solve the problem of demilitarizing Explosive D.

The previously unreported compound, 3-azidopicric acid (3-AzPA), is a precursor to a potential lead azide/lead styphnate replacement, 7-hydroxy-4,6-dinitrobenzofuroxan, potassium salt (KDNP). The synthesis to this new compound would be by diazotization of the known compound, 3-aminopicric acid (3-APA), followed by displacement of the diazo group by azide. The overall chemical transformation is shown below.

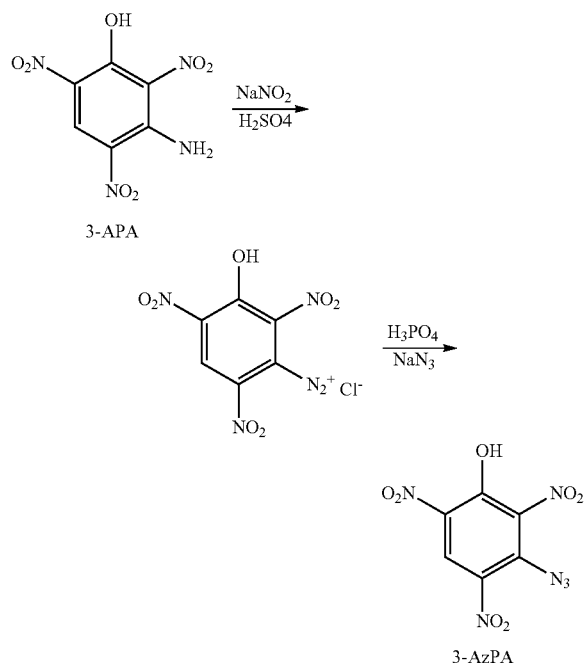

The present invention is the compound represented by the following formula

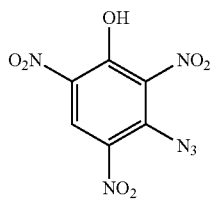

Chemical Formula: C₆H₂N₆O₇
Molecular Weight: 270.12.

General Synthesis

3-APA was slurried in concentrated H₂SO₄ in a 100 mL round bottomed flask and heated with stirring until homogeneous. The solution was then cooled in an ice bath to 0-5° C. A solution of NaNO₂ in concentrated H₂SO₄ was then added dropwise. Concentrated phosphoric acid was then added dropwise keeping the temperature between 0-10° C. NaN₃ was then added in portions at such a rate that the temperature does not exceed 5° C., and then allowed to come to room temperature. The reaction mixture was then poured into ice water. The resultant precipitate was then collected by filtration, dried and characterized.

Example 1

12 mL of concentrated sulfuric acid were charged to the flask depicted in the experimental setup, and agitation was initiated. 0.897 grams (0.0037 mol) of 3-APA was then added and rinsed down with an additional 3.5 mL of concentrated sulfuric acid. The 3-APA dissolved readily and heating the reaction mixture was unnecessary. The resultant solution was cooled to 3° C. using an ice water bath, and 0.39 grams (0.0057 mol) of NaNO₂ dissolved in 6 grams of concentrated sulfuric acid was added dropwise, keeping the temperature below 5° C. This addition took less than 5 minutes. The resultant solution was then stirred for 20 minutes at that temperature. 25 mL of phosphoric acid was then added at such a rate that the temperature did not exceed 5° C. This addition was somewhat exothermic and occurred over 45-50 minutes. After addition was complete, the reaction mixture was stirred at less than 5° C. for 10 minutes. During the addition and subsequent stirring, the reaction mixture became quite viscous and attained a pink-orange color. 1.18 grams (0.018 mol) of NaN₃ was then added in portions, keeping the temperature below 5° C. This addition took less than 5 minutes. The reaction mixture was then stirred at less than 5° C. for 20 minutes, and was then allowed to come to room temperature by removing the ice water bath. Once the reaction mixture had reached room temperature, it was poured into 70 mL of cold (<5° C.) water with stirring. The resultant yellow precipitate was then collected by filtration, and washed with 2×20 mL of cold water. The yellow solid exhibited some water solubility, so the water washed were retained for further analysis and/or crystal growth. The remaining precipitate was then dried in a dessicator, and yielded 0.44 grams (44% yield).

FTIR (Fourier Transform Infra-red Spectroscopy), DSC, NMR and preliminary small scale safety testing were performed on the solid. NMR data was consistent with the material being identified as 3-azidopicric acid, and FTIR data showed the characteristic absorbance for the azide functionality at 2144 cm$^{-1}$. The FTIR and DSC scans of the product, 3-AzPA are given in FIGS. 1 and 2, respectively. NMR data for 3-AzPA are $^1$H (acetone-d₆/TMS): 10.55 (1H, broad singlet); 9.09 (1H, singlet) ppm; $^{13}$C NMR (acetone-d₆/TMS): 125.7, 128.7, 131.7, 135.0, 135.8, 150.9 ppm

Experiment 2

Figure 4:
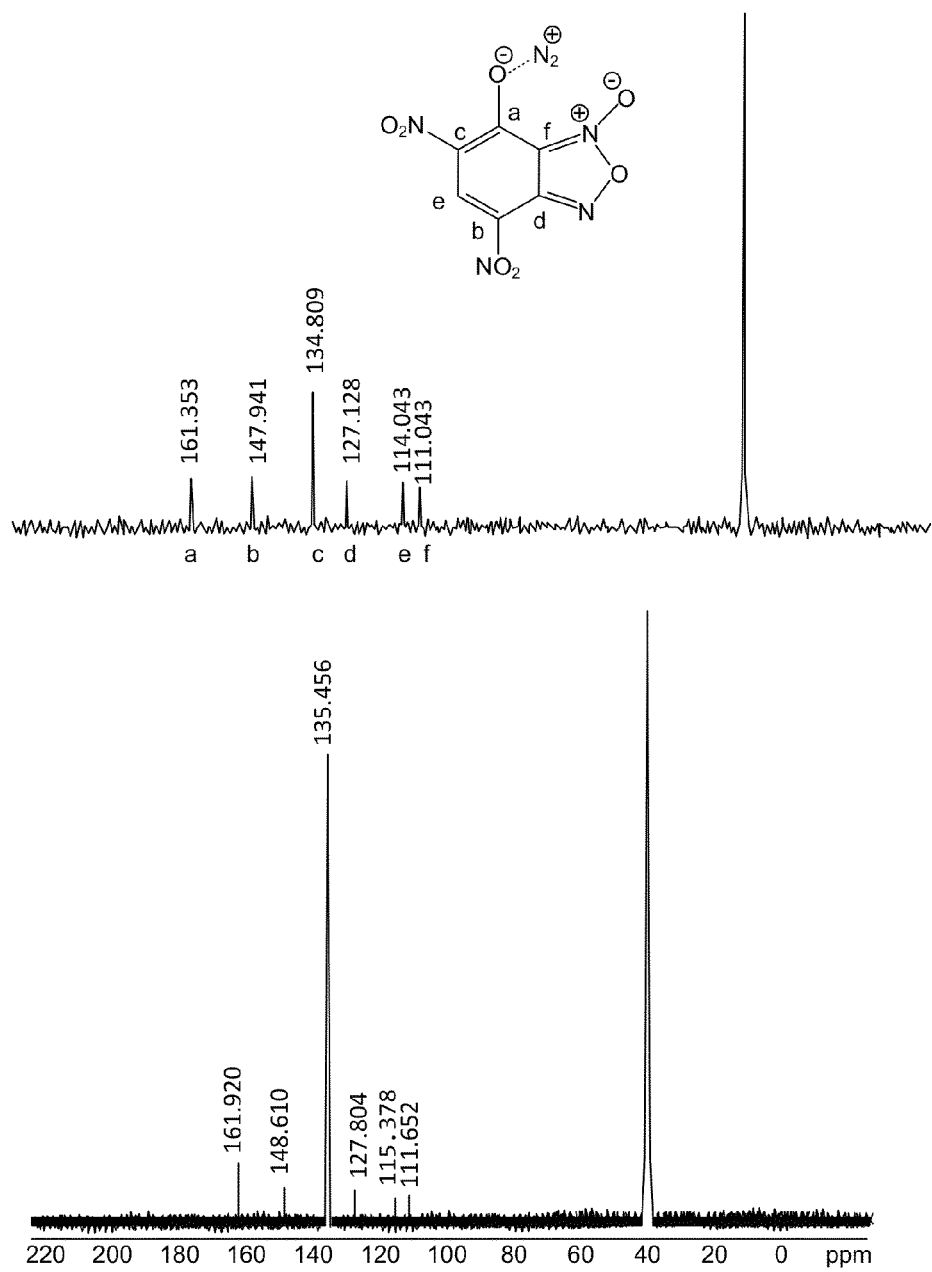
FIG. 4 is a comparative scan of a Nuclear Magnetic Resonance using $^{13}C$ for NaDNP vs. the scan of Experimental Procedure 2.
Figure 6:
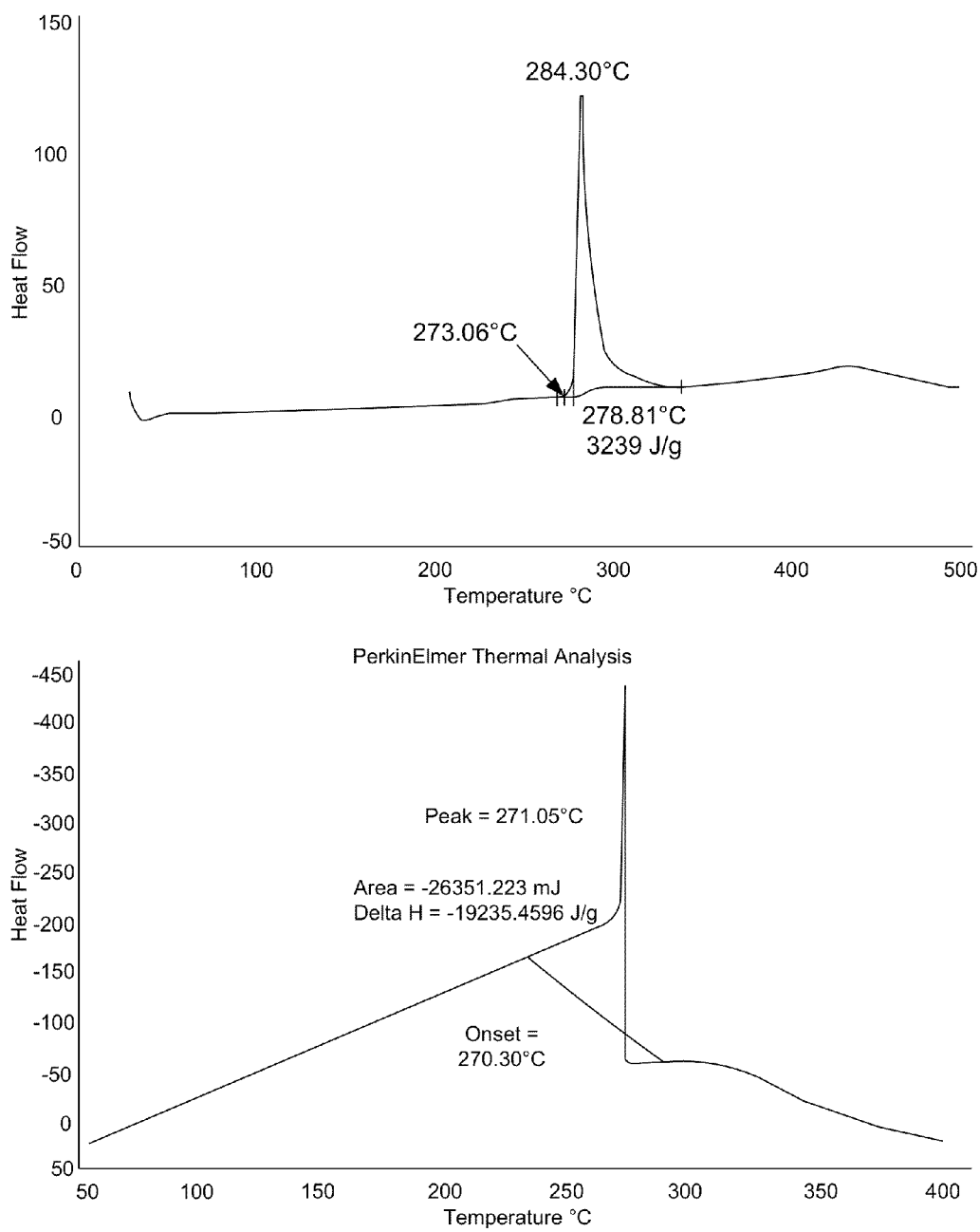
FIG. 6 is a comparative diagram of a Differential Scanning Calorimetry for a known sample of KDNP vs. the diagram of Experimental Procedure 2.

In an effort to confirm the intermediacy of 3-AzPA in a potential synthesis of KDNP, the preparation of the potassium salt of 3-AzPA was made. An aqueous solution of 3-AzPA was treated with potassium bicarbonate until evolution of gas ceased, and a dark red-brown precipitate formed immediately. The mixture was allowed to stand in the fume hood for 2 days while the volume decreased by approximately one third due to evaporation. The resultant solid precipitate was collected by filtration and dried under vacuum. Characterization of material by FTIR showed no evidence of a peak at ~2150 cm$^{-1}$, indicating that no azido group was present. Further characterization, and comparison with NMR data for the sodium analog of KDNP, as well as FTIR and DSC data for KDNP, led to the conclusion that the isolated material was KDNP. The comparative 1H and 13C NMR spectra are shown in FIGS. 3 and 4, respectively, the comparative FTIR scans are given in FIG. 5, and the comparative DSC scans are given in FIG. 6.

These data suggest that treatment of the aqueous 3-AzPA solution with potassium bicarbonate formed the intended potassium salt, which then underwent ring closure and loss of nitrogen to give KDNP at ambient temperature. The prior synthesis which converted 3-bromo-2,4,6-trinitroanisole to KDNP required high temperatures to effect this transformation.

Although the present invention has been illustrated and described herein with reference to exemplary embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. The compound 3-azidopicric acid which has the formula

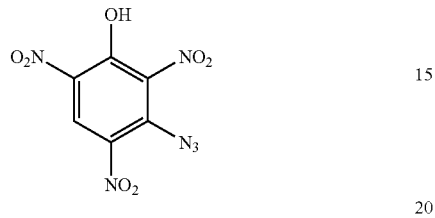

Chemical Formula: $C_6H_2N_6O_7$
Molecular Weight: 270.12.

2. A method of making 3-azidopicric acid, comprising:
   a) reacting 3-aminopicric acid with sulfuric acid and sodium nitrite,
   b) then reacting the result of step a) with phosphoric acid and sodium azide.

3. A method of making 4,6-dinitro-7-hydroxybenzofuroxan, potassium salt (KDNP) by treating an aqueous solution of 3-azidopicric acid with potassium bicarbonate.

* * * * *